(12) United States Patent
Kolde et al.

(10) Patent No.: US 9,329,192 B2
(45) Date of Patent: May 3, 2016

(54) POLYMER-COUPLED PEPTIDASES

(75) Inventors: Hans-Jurgen Kolde, Ottobrunn (DE); Ute Lange, Kahla (DE); Elke Bucha, Erfurt (DE)

(73) Assignee: SENOVA GESELLSCHAFT FUR BIOWISSENSCHAFT UND TECHNIK MBH, Weimar (DE)

( * ) Notice: Subject to any disclaimer, the term of this patent is extended or adjusted under 35 U.S.C. 154(b) by 269 days.

(21) Appl. No.: 13/026,474

(22) Filed: Feb. 14, 2011

(65) Prior Publication Data

US 2011/0201025 A1 Aug. 18, 2011

(30) Foreign Application Priority Data

Feb. 15, 2010 (EP) .................................. 10 15 3604

(51) Int. Cl.
| | | |
|---|---|---|
| *C12Q 1/56* | (2006.01) | |
| *G01N 33/86* | (2006.01) | |
| *C12N 9/74* | (2006.01) | |
| *C12N 9/64* | (2006.01) | |

(52) U.S. Cl.
CPC ................ *G01N 33/86* (2013.01); *C12N 9/647* (2013.01); *C12N 9/6429* (2013.01); *C12Y 304/21005* (2013.01)

(58) Field of Classification Search
CPC ................................ C12N 9/647; G01N 33/86
See application file for complete search history.

(56) References Cited

U.S. PATENT DOCUMENTS

| 6,060,300 | A | | 5/2000 | Raditsch et al. | |
|---|---|---|---|---|---|
| 7,220,553 | B2 | * | 5/2007 | Chu ................................. | 435/7.1 |
| 2009/0098119 | A1 | * | 4/2009 | Lu et al. .................... | 424/133.1 |

FOREIGN PATENT DOCUMENTS

| DE | 19904674 | | 8/2008 |
|---|---|---|---|
| EP | 2484776 | A1 * | 8/2012 |
| WO | 98/46648 | | 10/1998 |
| WO | 2006/134174 | A2 | 12/2006 |
| WO | WO 2008140220 | A1 * | 11/2008 |
| WO | 2009/042962 | A2 | 4/2009 |
| WO | WO 2014044703 | A1 * | 3/2014 |

OTHER PUBLICATIONS

Gulseth et al., Rivaroxaban: an oral direct inhibitor of factor Xa, 2008, American Journal of Health-System Pharmacy 65(16): 1520-1529.*
Lange et al., A simple and specific assay for direct factor Xa inhibitors in plasma without interference by heparins, Jan. 2010, Hamostaseologie 30(1): abstract P17-05.*
Datasheet for Pefabloc Xa, downloaded on Oct. 2014 from: http://www.pentapharm.com/files/391-03_DSe_Pefabloc%20tPA-Xa.pdf.*
Datasheet for S-2765, downloaded on Oct. 2014 from: http://www.diapharma.com/asp/productdetails.asp?ID=100400.*
Datasheet for rivaroxaban, downloaded on Oct. 2014 from: http://www.eurodiagnostico.com/media/pdf/Rivaroxaban%20(Xarelto).pdf.*
Sen et al., "Effect of glycoPEGylation on factor VIIa binding and internalization", Haemophilla, Bd. 16, Oct. 21, 2009, pp. 339-348, XP002573945.
Veronese FM., Pasut G., "PRGylation, successful approach to drug delivery", DDT, vol. 10, No. 21, Nov. 2005; pp. 1451-1458.

* cited by examiner

*Primary Examiner* — Robert Yamasaki
(74) *Attorney, Agent, or Firm* — Ann Wieczorek; Mayer & Williams PC

(57) ABSTRACT

The present invention is directed to a simple process for the modification of the specificity of a peptidase of the hemostatic system by coupling polymers to the peptidase causing it to lose its reactivity in the hemostatic system, but enabling it to continue to react with certain inhibitors, effectors and substrates. The invention is furthermore directed to processes for the detection or quantitative determination of inhibitors of the peptidase in bodily fluids or other samples as well as to processes for their neutralization and/or removal from liquids. Finally, the invention allows the use of a polymer-coupled peptidase as drug and furthermore provides a device which makes use of such a peptidase in the removal of peptidase inhibitors from samples or from the bloodstream of a patient.

25 Claims, 6 Drawing Sheets

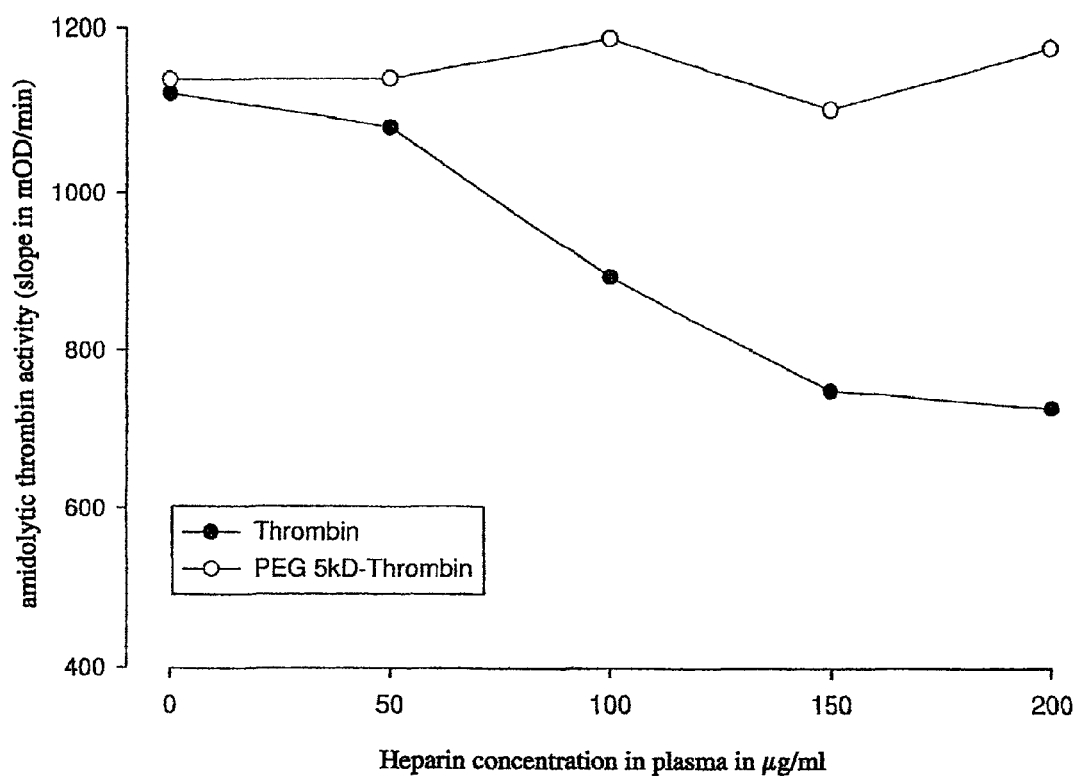

POLYMER-COUPLED PEPTIDASES

FIELD OF THE INVENTION

The present invention is directed to a simple process for the modification of the specificity of a peptidase of the hemostatic system. Simply by coupling polymers to the peptidases, it modifies the specificity of the peptidases such that they lose their reactivity in the hemostatic system, in particular with macromolecular physiological receptors, substrates, cofactors and inhibitors, but they continue to be able to react with certain inhibitors, effectors and substrates.

By applying this process, the invention furthermore provides methods for the detection or quantitative determination of inhibitors of the peptidases of the hemostatic system in bodily fluids or other samples, as well as methods for their in vivo or in vitro neutralization and/or in vitro or in vivo removal from bodily fluids or other samples. Finally, the invention provides polymer-coupled peptidases for use in the processes of the present invention and as drugs, and a device which makes use of such conjugates in the removal of peptidase inhibitors from samples or from the bloodstream of a patient.

BACKGROUND OF THE INVENTION

Peptidases (also referred to as proteinases or proteases) are enzymes which catalyze the cleavage of peptide bonds in peptides or proteins. In the form of endopeptidases, they prefer as reactants peptide bonds within the target molecule which generally involve specific amino acids. Other peptidases cleave individual or several amino acids from the N- or C-terminus of the protein. Depending on their tertiary structure, the different endopeptidases are often able to react with different physiological or unphysiological reactants of different molecular size comprising different specific peptide bonds.

Peptidases fulfill important functions in the organism and are involved in the physiological, but also pathological, procedures of numerous processes such as e.g., the breakdown of proteins, immune response (complement system), blood coagulation and fibrinolysis.

In addition, in some cases the activated endopeptidases also form macromolecular complexes with cofactors, such as e.g., the activated coagulation factor Xa with factor Va in the prothrombinase complex.

However, for certain diagnostic as well as therapeutic processes, this spectrum of reactants is disadvantageous for a purposeful, specific use of such enzymes.

The process of blood coagulation is very complex and involves several steps whereby inactive enzyme precursors are activated by a combination of enzymatic action and cofactors which results in active coagulation enzymes.

For balancing the equilibrium between the coagulation tendency of the blood and safeguarding its flow properties within the circulation, there is also another interconnected system of inhibiting or amplifying interactions with additional molecules which is regulated by numerous positive and negative feedback mechanisms.

New classes of drugs have been and are being developed for the treatment of defects of the blood coagulation system, which specifically only inhibit a single enzyme of the coagulation cascade, such as e.g., the activated factor Xa (active ingredient class of direct factor Xa inhibitors e.g., Rivaroxaban®, Apixaban®, Betrixaban®, Otamixaban®, Edoxaban®, Eribaxaban, YM150, LY-517717, PRT054021 and others) or thrombin (active ingredient class of direct thrombin inhibitors, e.g., Dabigatran®, Argatroban, Bivalirudin, MCC-977, AZD0837, NU172, Flovagatran and others).

In order to guarantee an effective (prevention of thrombosis) and safe therapy (prevention of bleeding) with such drugs, both the availability of exact methods for detecting the active ingredient in bodily fluids as well as the possibility of neutralizing or removing these drugs are of the utmost importance.

In order to be able to purposefully measure or neutralize drugs in vitro or in vivo which inhibit specific enzymes of the hemostatic system, it would be highly advantageous if the spectrum of possible reaction of the various enzymes could be modified or limited.

Accordingly, modifications of the molecular structure of thrombin and factor Xa have become known in the course of the development of antidotes to factor Xa and thrombin inhibitors which cause these peptidases to lose their ability to function and interact in the coagulation system while continuing to interact with the specific inhibitor substances. Such modified peptidases are intended to be used to neutralize the active ingredient. "Neutralization" herein refers to a binding of the active ingredient molecule to the peptidase which leads to the inability of the active ingredient molecule to perform its function as an inhibitor of the hemostatic system. This may be achieved by removing and/or exchanging specific amino acids. Documents U.S. Pat. No. 6,060,300 (Thrombin muteins as antidotes for thrombin inhibitors) and WO 2009/041962 (Antidotes for Factor Xa inhibitors and methods of using the same), inter alia, disclose intricate processes for this purpose. In addition, US 2009/0098119A1 discloses that the inherently short half life of the mutants of factor Xa can be extended by a reaction with polyethylene glycol, but not that other properties of the mutated factor Xa molecule are changed due to this modification.

SUMMARY OF THE INVENTION

The present invention provides a simple process for modifying the specificity of peptidases of the hemostatic system, such as e.g., peptidases of the coagulation system, in particular for the purpose of using the thus modified peptidases for the detection or neutralization of drugs which act as inhibitors of peptidases of the coagulation system. In particular, the present invention provides modified peptidases which can react with the inhibitors and substrates to be detected or neutralized, but which at the same time lose or essentially lose the ability to react within the coagulation system.

The present invention provides a method for the detection or quantitative determination of an inhibitor of a peptidase of the hemostatic system in a sample, comprising the steps of bringing the inhibitor in the sample into contact with a polymer-coupled peptidase of the hemostatic system, wherein the specificity of the peptidase is modified via the polymer coupling such that the peptidase loses its reactivity in the hemostatic system, but is still able to react with inhibitors and substrates of low molecular weight, and measuring the activity of the polymer-coupled peptidase after it has been brought into contact with the inhibitor in the sample.

The method of the present invention can further comprise the step of comparing the activity of the polymer-coupled peptidase measured after it has been brought into contact with the sample with one or more reference values of the activity of the polymer-coupled peptidase. In addition, one or more reference values can be obtained from samples containing the polymer-coupled peptidase without the inhibitor and/or together with known concentrations of the inhibitor. The sample is a bodily fluid, selected from blood, plasma, serum, liquor and sweat. The inhibitor may be a direct inhibitor of the peptidase, preferably an inhibitor with a molecular weight between 100 and 7,500 Da. Further, the inhibitor can be an active ingredient of the classes of direct factor Xa inhibitors or direct thrombin inhibitors.

In some embodiments according to the invention, the peptidase of the hemostatic system is a coagulation factor selected from the group consisting of factor IIa (thrombin), VIIa, IXa, Xa, XIa and fragments and mutants of these factors. The peptidase of the hemostatic system, in some embodiments, is factor IIa (thrombin) or factor Xa.

In some embodiments, the polymer can be a polyalkylene glycol or a copolymer comprising alkylene glycol units. In some embodiments, the polymer is polyethylene glycol or a copolymer comprising ethylene glycol units.

In another aspect, the present invention is directed to a test kit for carrying out the above-described method, comprising as a first reagent a polymer-coupled peptidase of the hemostatic system and as a second reagent a substrate of the peptidase.

In another aspect, the present invention is directed to a method for the complete or proportional inhibition of the activity of an inhibitor of a peptidase of the hemostatic system, comprising the step of bringing a sample containing the inhibitor into contact with a polymer-coupled peptidase of the hemostatic system, wherein the specificity of the peptidase is modified via the polymer coupling such that the peptidase loses its reactivity in the hemostatic system, but is still able to react with inhibitors and substrates of low molecular weight. The sample is taken from the blood of a patient who is being or has been treated with a drug containing an inhibitor of a peptidase of the hemostatic system as an active ingredient and after the sample has been brought into contact with the coupled peptidase, the inhibitor administered with the drug is bound by the peptidase and thus neutralized. Additionally, after neutralization of the inhibitor, tests are carried out on the sample in order to diagnose defects in the hemostatic system or to determine the activity of substances which interfere with the hemostatic system. The sample can be a bodily fluid, selected from blood, plasma, serum, liquor and sweat. The inhibitor can be a direct inhibitor of the peptidase, preferably an inhibitor with a molecular weight between 100 and 7,500 Da. The peptidase of the hemostatic system can be a coagulation factor selected from the group consisting of factor IIa (thrombin), VIIa, IXa, Xa, XIa and fragments and mutants of these factors. The polymer can be a polyalkylene glycol or a copolymer comprising alkylene glycol units.

In some embodiments, a defined amount of the polymer-coupled peptidase is added to the sample to achieve a proportional neutralization of the inhibitor by contacting the inhibitor in a sample with the polymer coupled peptidase, and the remaining activity of the inhibitor in the sample as a measure for the initial concentration is determined in terms of the influence of the inhibitor on the coagulation tendency by carrying out a coagulation test in the sample, including the addition of a coagulation activator and optionally, normal plasma as a source for additional coagulation factors and fibrinogen. The complete or proportional neutralization of the inhibitor of a peptidase of the hemostatic system is carried out in order to achieve a restoration of the coagulation ability of the blood of a patient who has been treated or is being treated with a pharmaceutical composition containing an inhibitor of a peptidase of the hemostatic system, and the neutralization comprises contacting the polymer-coupled peptidase with the inhibitor in the circulation of the patient.

BRIEF DESCRIPTION OF THE DRAWINGS

FIG. 6: Influence of the concentration of heparin in plasma on the amidolytic activity of PEG 5 kD-thrombin conjugate and non-modified thrombin, respectively.

DETAILED DESCRIPTION OF THE INVENTION

Figure 1:
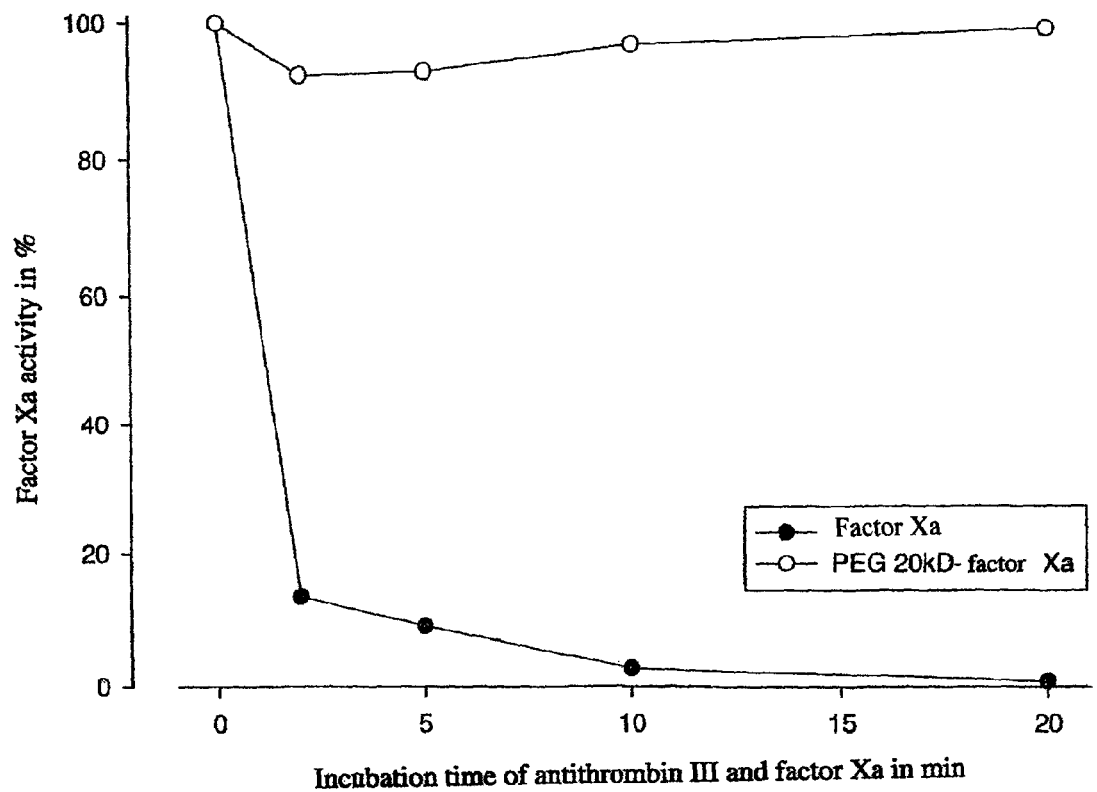
FIG. 1: Influence of incubation with antithrombin III on the activity of PEG 20 kD-factor Xa conjugate and non-modified factor Xa, respectively.

It has surprisingly been found that peptidases of the hemostatic system or coagulation system, such as factor Xa or thrombin, lose their reactivity within the coagulation system after coupling to one or more polymers, in particular polyalkylene glycols and copolymers comprising alkylene glycol units, but at the same are still able to react with inhibitors and substrates of low molecular size. Hereinafter, the modified peptidases of the hemostatic system according to the present invention are also referred to as "polymer-coupled" peptidases for the sake of simplification.

The peptidase which is coupled with one or more polymers according to the present invention is a peptidase of the hemostatic system, in particular the hemostatic system of a mammal such as a human. It can be obtained in different manners and encompasses both recombinant peptidases and peptidases obtained from organisms, in particular blood, as well as their fragments or mutants. Mutants of the peptidases differ from the corresponding native peptidases in that one or more, preferably 1 to 10 amino acids groups have been deleted or inserted or replaced with one amino acid residue each. They can be provided by known processes such as for example synthetic processes or site-directed mutagenesis. Ideally, the fragments and mutants of the peptidases mentioned herein show at least 80%, more preferably 90%, of the biological activity and especially the same biological activity as the corresponding native peptidase, wherein the activity can be determined by means of processes known in the technical field. This means that, if they are not coupled to a polymer, the corresponding fragment or mutant preferably show the same physiological effect and interact with the same substances as the corresponding native peptidase, resulting in the same biological effect.

Preferably, the peptidase of the hemostatic system is a coagulation factor in its activated form, in particular a coagulation factor selected from factor IIa (thrombin), VIIa, IXa, Xa and XIa. Thrombin and factor Xa are especially preferred. The use of a native form of the proteinases for coupling to one or more polymers is also preferred.

The polymers to be coupled to such peptidases in accordance with the present invention are chemical compounds comprising molecule chains and/or branched molecules which preferably consist of identical or similar units. They include synthetic polymers such as e.g., polyalkylene glycols or biopolymers, such as e.g., molecules with repeating amino acid sequences or carbohydrate units which can optionally be derivatized by substitution. Examples include dextran or hydroxyethyl starch. In the pharmaceutical industry, some of these polymers are coupled to active ingredients in order to extend their half life in the organism. For example, PEGylation, HESylation and PASylation are such processes.

The polymer which is coupled to a peptidase of the hemostatic system according to the present invention usually has an average molecular weight (weight average) of at least 1,000 Da, preferably at least 2,000 Da and in particular at least 5,000 Da. Moreover, the molecular weight is usually at most 60,000 Da, preferably at most 40,000 Da and in particular at most 20,000 Da.

The polymer can be branched or linear; linear polymers are preferred.

Preferably, the polymer of the polymer-coupled peptidase is a polyalkylene glycol or a copolymer comprising alkyleneglycol units. The alkylene portion of the alkylene glycol units of the polyalkylene glycol or the copolymer preferably comprises 1 to 6, especially preferred 2 or 3 carbon atoms. Copolymers preferably comprise at least 50 mol %, especially preferred at least 70 mol % and particularly preferred at least 90 mol %, based on the total amount of repeating units in the copolymer, of repeating units of the formula -Alk-O—, wherein "Alk" represents an alkylene group as defined above.

It is especially preferred that the polymer be a polyethylene glycol (also referred to as PEG) or a copolymer comprising ethylene glycol units. Copolymers preferably comprise at least 50 mol %, especially preferred at least 70 mol % and particularly preferred at least 90 mol %, based on the total amount of repeating units, of repeating units of the formula —$CH_2$—$CH_2$—O—.

In a further preferred embodiment, the peptidase is the coagulation factor Xa and the polymer is polyethylene glycol with an average molecular weight (weight average) of usually at least 1,000 Da, preferably at least 2,000 Da and in particular at least 5,000 Da. Moreover, the average molecular weight is usually at most 60,000 Da, preferably at most 40,000 Da and in particular at most 20,000 Da. In another preferred embodiment, the peptidase is the coagulation factor thrombin and the polymer is polyethylene glycol with an average molecular weight (weight average) of usually at least 1,000 Da, preferably at least 2,000 Da and in particular at least 5,000 Da. Moreover, the average molecular weight is usually at most 60,000 Da, preferably at most 40,000 Da and in particular at most 20,000 Da.

The polymer is preferably coupled to the peptidase by means of a covalent bond which can be created using standard chemical processes. Usually, for this purpose the polymer is activated at a terminus in order to enable it to react with a functional group of the peptidase. In the case of a polyalkylene glycol, known reactive derivatives such as for example succinimidyl succinate, succinimidyl propionate, nitrophenyl carbonate, tresylate, epoxides, aldehydes, isocyanates, maleimides and the like can be used (Veronese FM, Pasut G: PEGylation, successful approach to drug delivery. DDT 2005; 10:1451-1458). A peptidase molecule can be coupled to one or more polymer molecules, for example 1 to 10 polymer molecules. The molar ratio of peptidase/polymer is controlled by the amounts used in the coupling reaction.

It has been found that by coupling the peptidase to the polymer, the specificity, i.e. in particular the substrate specificity of the peptidase, is modified such that the peptidase loses its reactivity in the hemostatic system or that the reactivity is significantly reduced. In particular, it loses its reactivity with macromolecular physiological receptors, macromolecular substrates, macromolecular cofactors and macromolecular inhibitors. Such macromolecular physiological receptors, macromolecular substrates, macromolecular cofactors and macromolecular inhibitors are often proteins and polypeptides. In this connection, the loss or the significant reduction of reactivity in the hemostatic system means for example that the peptidase is no longer or only to a minimum extent able to fulfill its physiological function and/or to convert the mentioned macromolecular substrates. For instance, in the case of polymer-coupled coagulation factors, this is demonstrated by the fact that in a commercially available plasma deficient in the corresponding coagulation factor (e.g., abnormal plasma, American Diagnostica Inc.), they do not affect the prothrombin time of this defective plasma caused by the lack of this factor, while the addition of an unmodified peptidase of the coagulation system leads to a shortening up to a normalization of the prothrombin time of the plasma. Coagulation assays known in the art also show that the polymer-coupled peptidases do not cause a shortening of the coagulation time as an indication of a coagulation effect in plasma samples.

For example, by means of the polymer-coupling, the reactivity of a peptidase with macromolecular substances of the hemostatic systems with a molecular weight of 30,000 Da and higher can be suppressed or significantly reduced.

This way, the polymer coupling not only causes the peptidase to lose the ability of reacting with the reactants of the coagulation cascade, but they also can no longer be inhibited by physiological inhibitors such as e.g., antithrombin with a molecular weight of 58,000 Da (in particular for PEG-Xa, PEG-IIa) or tissue factor pathway inhibitor with a molecular weight of 39,000 Da (in particular for factor Xa).

On the other hand, the coupling with the polymer does not affect the ability of the peptidase to react with low molecular weight substrates or low molecular weight inhibitors of the peptidase of the hemostatic system. In this connection, the reaction with an inhibitor of the peptidase results in an inhibition of the activity of the polymer-coupled peptidase. Depending on the concentration ratio of peptidase and inhibitor, this inhibition can be a partial or a complete inhibition. In this context, the term "activity of the polymer-coupled peptidase" in particular denotes its ability to enzymatically convert substrates. Since, as was described above, the reactivity of the peptidase with macromolecular substrates is no longer given due to the coupling with the polymer, it usually refers to the ability to enzymatically convert low molecular weight substrates. A substrate with a molecular weight of at least 100 Da and at most 10,000 Da is preferred. More preferably, the molecular weight of the low molecular weight substrate is at most 7,500 Da, in particular at most 5,000 Da or at most 2,500 Da.

Inhibitors of peptidases of the hemostatic system, which are also effective as inhibitors of the polymer-coupled peptidases according to the present invention, are usually directly interacting or directly binding inhibitors or directly binding coagulation inhibitors, in particular those that are used as drugs for this purpose.

Usually, the inhibitors of the hemostatic system which react with the polymer-coupled peptidases or are neutralized by them are low molecular weight inhibitors. Again, an inhibitor with a molecular weight of at least 100 Da and at most 10,000 Da is preferred. More preferred, the molecular weight of the inhibitor is at most 7,500 Da, in particular at most 5,000 Da or at most 2,500 Da. Examples of such inhibitors include active ingredients selected from the group of active ingredients of the drugs for the direct inhibition of coagulation factor Xa such as rivaroxaban, apixaban, betrixaban, otamixaban, edoxaban, raxazaban, eribaxaban, YM150, LY-517717 or PRT054021, or for the direct inhibition of thrombin such as dabigatran, argatroban, flovagatran, AZD0837, MCC-977, NU172 or bivalirudin. Active ingredients for the direct inhibition or direct inhibitors are those substances which exert their inhibiting activity via a direct interaction with the coagulation factor, i.e. typically a binding to the corresponding coagulation factor.

In a preferred embodiment for the provision of a polymer-coupled peptidase, the peptidase is coupled to PEG according to known processes. Here, reactive PEG derivatives such as for example succinimidyl succinate, succinimidyl propionate, nitrophenyl carbonate, tresylate, epoxides, aldehydes, isocyanates, maleimides and the like can be used (Veronese FM, Pasut G: PEGylation, successful approach to drug delivery. DDT 2005; 10:1451-1458).

The number of chains to be coupled as well as their length can be chosen as desired and adapted to the enzyme structure in question wherein average molecular weights of the PEG chains as mentioned above are preferred. In order to completely deactivate the reactivity of peptidases with components of the coagulation system, PEG molecules of at least 5,000 Da are preferably used for coupling.

This way, factor Xa can for example be coupled to PEG such that the resulting PEG-Xa is no longer able to interact with the prothrombinase complex (cofactor Va, phospholipid) and to cleave the proenzyme prothrombin to form active thrombin, the enzyme essential for triggering coagulation at the end of the coagulation cascade. PEG-Xa also loses its ability to react with the physiological macromolecular inhibitors of factor Xa such as antithrombin or TFPI (tissue factor pathway inhibitor).

However, after the PEG coupling to factor Xa, the original reactivity of factor Xa with the low molecular inhibitors used inter alia as active ingredients in drugs is surprisingly maintained, as is its reactivity with low molecular peptide substrates.

One embodiment of the present invention, wherein the polymer-coupled peptidases described above are used, is a method for the detection or quantitative determination of an inhibitor of a peptidase of the hemostatic system in a sample, comprising bringing the inhibitor in the sample into contact with a polymer-coupled peptidase of the hemostatic system and measuring the activity of the coupled peptidase after it has been brought into contact with the inhibitor in the sample. The detection or quantitative determination can then easily be completed e.g., by comparing the activity of the coupled peptidase, after it has been brought into contact with the sample, with one or more reference values for the activity of the polymer-coupled peptidase. Thus, it is for example possible to determine a possible inhibition of the activity. As set out in detail below, such (a) reference value(s) of the activity of the polymer-coupled peptidase can be obtained by measuring the activity of the polymer-coupled peptidase in samples containing the polymer-coupled peptidase together with known concentrations of the inhibitor, or in samples without the inhibitor.

Alternatively, the detection or quantitative determination can be completed by measuring the coagulation time of the sample after it has been brought into contact with the coupled peptidase, and comparing the coagulation time with one or more reference values in order to determine a possible change in the coagulation time. Such a change is caused by the reaction of the inhibitor with the coupled peptidase which leads to an inhibition of the inhibitor activity.

The method for the detection or quantitative determination of an inhibitor of a peptidase of the hemostatic system in a sample is especially suitable for the detection or quantitative determination of a low molecular weight inhibitor. Again, an inhibitor with a molecular weight of at least 100 Da and at most 10,000 Da is preferred. Preferably, the molecular weight of the inhibitor is at most 7,500 Da, in particular, at most 5,000 Da or at most 2,500 Da. Examples of such inhibitors are mentioned above. It should be apparent for the person skilled in the art that, as a rule, the polymer-coupled peptidase used in the process of the present invention should be adapted to the inhibitor to be detected or quantitatively determined, i.e. a peptidase should be selected which is basically able to interact with the inhibitor. Preferably, for the detection or quantitative determination of a low molecular weight inhibitor within the framework of the present invention, a polymer-coupled peptidase should be used on which the inhibitor acts as a direct inhibitor.

In particular, the process for the detection or quantitative determination can comprise the following preliminary steps:
(a) providing at least one sample in which an inhibitor is supposed to be present; and
(b) bringing at least one sample from (a) into contact with a polymer-coupled peptidase according to the present invention as described above.

Samples obtained in step (a) can also be used for the detection or quantitative determination of the inhibitor according to the alternative above which involves measuring the coagulation time, not only as measuring sample in step (b), but also as reference samples, e.g., for measuring a coagulation time without the addition of the PEG-coupled peptidase.

Typically, bringing the coupled peptidase into contact with the inhibitor according to the present invention encompasses an incubation of the sample with the coupled peptidase. This is accomplished e.g., in step (b) above during which an interaction of an inhibitor possibly present in the sample with the coupled peptidase can take place.

The sample is usually a sample comprising a liquid or a sample which is a liquid. It is frequently a biological sample, for example a bodily fluid such as blood, plasma, serum, liquor, urine or sweat, preferably blood or plasma. The sample can for example be a sample for a measuring or diagnostic method.

A reference value of the activity of the polymer-coupled peptidase for comparison with the activity of the polymer-coupled peptidase in the sample can be generated, e.g., by measuring the activity of the polymer-coupled peptidase without prior contact with an inhibitor. A reduction of the activity of the coupled peptidase after it has reacted with an inhibitor in the sample compared to such a reference value allows the conclusion that the inhibitor was present in the sample. Also, several reference values can be generated for the comparison by measuring the activity of the coupled peptidase after contact with different known concentrations of an inhibitor. Thus, a comparison with the reference values allows for example a quantitative determination of the inhibitor. In these cases, an excess amount of polymer-coupled peptidase compared to the assumed amount of inhibitor to be determined may be used such that the activity of the polymer-coupled inhibitor is reduced proportionally to the amount of inhibitor present.

The measurement of the activity of the polymer-coupled peptidase, to generate one or more reference values and also after it was contacted with the sample to generate the measured value which provides information about the presence or the concentration of the inhibitor in the sample, can be carried out according to conventional methods. What is determined in general is the ability of the polymer-coupled peptidase to enzymatically convert substrates. Since, as was described above, the reactivity of the peptidase with macromolecular substrates is no longer a given due to the coupling with the polymer, the activity of the polymer-coupled peptidase usually refers to the ability to enzymatically convert low molecular weight substrates. A substrate with a molecular weight of at least 100 Da and at most 10,000 Da is preferred. More preferably, the molecular weight of the substrate is at most 7,500 Da, in particular at most 5,000 Da or at most 2,500 Da.

The activity of the polymer-coupled peptidase can be measured, e.g., via the cleavage of a detectable group from a suitable substrate, typically via photometric, spectrophotometric, fluorescence-spectrometric or electrochemical methods. For example, known substrates can be used from which the peptidase can cleave a signal-generating group, such as e.g., a chromogenic substrate. Examples of suitable commercially available chromogenic substrates for peptidases include, for factor Xa, N-α-Z-D-Arg-Gly-Arg-pNA (e.g., S-2765™, Chromogenix Instrumentation Laboratory, Milano, Italy), and for thrombin H-D-Phe-Pip-Arg-pNA (S-2238™, Chromogenix Instrumentation Laboratory, Milano, Italy); alternatively, fluorigenic, luminogenic or electrochemical substrates can, for example, also be used together with a corresponding detection technology.

According to the alternative mentioned above, the inhibitor in the sample can also be determined based on the measurement of the coagulation time. There are different possible methods. For a mere detection, it is usually sufficient to determine that the coagulation time of a sample that has been in contact with the polymer-coupled peptidase is shorter than the coagulation time of a corresponding sample without contact with the coupled peptidase (reference value) due to a complete or proportional neutralization of the inhibitor.

For a quantitative determination, a corresponding comparison of two samples or two groups of samples can be relied on wherein in one sample the inhibitor has been neutralized by the addition of the coupled peptidase. The observed change in the coagulation time in the neutralized versus the non-neutralized samples can subsequently be compared with a calibration curve showing the changes in the inhibitors caused by known concentrations. In a specific embodiment of the alternative using the measurement of the coagulation time, the inhibitor present in the sample can be proportionally neutralized by the addition of a defined amount of the polymer-coupled peptidase. In this case, a defined amount of polymer-coupled peptidase may be used which may neutralize only a part of the inhibitor present. Then, a coagulation activator such as e.g., thromboplastin, partial thromboplastin, coagulation-activating snake poison or a coagulation-activating protease isolated therefrom, or an activated coagulation factor which comes before the inhibited enzyme in the activation cascade, can be added to this sample. In this case, the coagulation time is extended in the sample in which the inhibitor is to be determined due to the residual concentration of the inhibitor compared to a corresponding sample without inhibitor. When this value is compared with the coagulation time measured in a same sample material without the addition of the coupled peptidase but with the addition of known concentrations of a suitable calibrator, the concentration of the inhibitor can be determined using a suitable calibration and excluding the influence of the sample composition.

If, due to its composition, the sample material is unable to coagulate, normal plasma can for example be added as a source for other coagulation factors for the coagulation measurement of option (ii), or in particular fibrinogen, which further increases the specificity of the process.

The method for the detection or quantitative determination according to the first embodiment can e.g., be an in vitro diagnostic process, in particular for the detection or quantitative measurement of an inhibitor of a peptidase of the hemostatic system in a biological sample such as blood, plasma, serum, liquor, urine or sweat. However, the process can also be used in other samples, such as aqueous solutions, e.g., in screening processes when searching for an active ingredient.

In particular, e.g., within the framework of an in vitro diagnostic process, the sample can be from a mammal such as e.g., a human.

A preferred embodiment for the detection or quantitative determination of an inhibitor of a peptidase in the hemostatic system allows a specific detection of coagulation-inhibiting drugs whose active ingredient is a direct factor Xa inhibitor in bodily fluids such as blood, plasma, serum, liquor, urine, sweat, or other liquids. Due to the specificity of the polymer-coupled factor Xa, in particular PEG-coupled factor Xa (in the following also referred to as "Polymer-Xa" or "PEG-Xa") for direct factor Xa inhibitors, the process according to the present invention provides exact evidence as to the active ingredient concentration without distortion of the result due to the influence of the current functional condition of the coagulation system. Also, indirect factor Xa inhibitors, which function, for example, via antithrombin, such as unfractionated or low molecular weight heparins, orgaran or pentasaccharides such as fondaparinux bear no influence, either. This aspect is advantageous because patients are often switched from heparins to direct parenteral or oral anticoagulants and therefore both classes of active ingredients are present in their bloodstream during the transitional period. Those are therefore detected to a larger or lesser extent in the previously known determination methods.

For carrying out this preferred method according to the present invention, a defined amount of polymer-coupled Xa, in particular PEG-Xa, is added to a sample, e.g., plasma, containing a directly acting factor Xa inhibitor and incubated for a suitable period of time. It is advantageous to use an excess of the polymer-coupled peptidase, compared to the expected amount of the inhibitor. The polymer-Xa or PEG-Xa binds the inhibitor and is proportionally deactivated. Then, the activity of the polymer-coupled peptidase is measured, e.g., a substrate can be added from which the non-deactivated polymer-Xa or PEG-Xa can cleave a signal-generating group, such as e.g., a chromogenic substrate.

The residual activity of polymer-Xa or PEG-Xa, which correlates inversely with the concentration of the inhibitor, cleaves the chromogenic substrate. The resulting developing color is measured using a suitable process. By using a suitable calibration, the concentration of the inhibitor in the sample can be measured exactly while the influence of the sample composition is excluded, in particular also in the presence of indirect inhibitors, such as heparins. In addition to particularly low molecular weight chromogenic substrates, fluorigenic, luminogenic or electrochemical substrates, low molecular fluorigenic, luminogenic or electrochemical substrates can, for example, also be used together with a corresponding detection technology.

The fundamental nature of the process for the modification of the specificity of a peptidase of the hemostatic system by coupling to polymers such as polyethylene glycol can also be illustrated using thrombin as an example (hereinafter also referred to as polymer thrombin or PEG thrombin). In its polymer-coupled form, in particular by coupling with PEG, thrombin loses its ability to interact with components of the coagulation system and thus its function in the coagulation system. It is no longer able to cleave fibrinogen to form fibrin and thus induce coagulation in a plasma or blood sample. Polymer thrombin, in particular PEG thrombin, cannot react with other components of the plasmic or cellular coagulation system, nor with physiological inhibitors such as antithrombin, heparin cofactor II or α2-macroglobulin.

However, the polymer thrombin, in particular PEG thrombin, retains the reactivity with direct low molecular weight thrombin inhibitors with a preferred molecular weight of at least 100 Da and at most 7,500 Da, as well as the reactivity with low molecular weight peptide substrates with corresponding molecular weights.

Thus, analogous to the preferred process for measuring factor Xa inhibitors, a process for measuring direct low molecular weight thrombin inhibitors can, for example, be carried out as well. Polymer thrombin, in particular PEG thrombin, binds the inhibitor contained in the sample and is thus proportionally deactivated. Its residual activity, which correlates inversely with the concentration of the inhibitor in the sample, is measured with suitable low molecular substrates, e.g., by determining the color intensity after reaction with a chromogenic substrate. By using a suitable calibration, the concentration of the inhibitor can be determined.

Due to the properties of the polymer-coupled, in particular PEG-coupled peptidases, preferred methods for measuring the concentration of direct inhibitors of factor Xa and thrombin can be established as well which, as was described above, are based on a measurement of the coagulation time. For this purpose, the inhibitor present in the sample is proportionally neutralized by the addition of a defined amount of the PEG peptidase. If suitable coagulation activators such as e.g., thromboplastin, partial thromboplastin, coagulation-activating snake venom or a coagulation-activating protease isolated therefrom, or an activated coagulation factor which comes before the inhibited peptidase in the activation cascade, are then added to this sample, the coagulation time is extended due to the residual concentration of the active ingredient. When this value is compared with the coagulation time measured in the same sample material without the addition of the PEG enzyme but with the addition of known concentrations of a suitable calibrator, the concentration of the coagulation inhibitor can be determined excluding the influence of the sample composition. If, due to its composition, the sample material is unable to coagulate, normal plasma can, for example, be added as a source for other coagulation factors and in particular fibrinogen, which further increases the specificity of the process.

In addition to factor Xa and thrombin, processes based on these principles are also possible for other peptidases of the hemostatic system or their inhibitors, such as, for example, for factors IXa, XIa and VIIa.

In another related embodiment, the present invention also relates to devices, drugs and processes for the neutralization of inhibitors of peptidases of the hemostatic system, whereby the term "neutralization" is to be understood such that the inhibitor is bound by a reaction with the coupled peptidase according to the present invention and thus no longer exhibits any inhibiting activity in a sample or an organism.

In particular, the present invention encompasses a method, which may be an in vitro or in vivo method, for neutralizing the inhibitor activity of an inhibitor of a peptidase of the hemostatic system, comprising bringing into contact a sample comprising the inhibitor with a polymer-coupled peptidase as described above. The sample is usually a sample comprising a liquid or a sample which is a liquid. It is frequently a biological sample, for example a bodily fluid such as blood, plasma, serum, liquor, urine or sweat, preferably blood or plasma. In one embodiment, this method is applied within the framework of an in vitro diagnosis wherein a sample is taken from a mammal, in particular a human, but not returned to the subject.

Upon contact of the inhibitor with the polymer-coupled peptidase, the inhibitor can be bound and thus neutralized by the polymer-coupled peptidase. Depending on the relative amounts of inhibitor and polymer-coupled peptidase, the neutralization may be complete (i.e. all inhibitor molecules are neutralized) or proportional to the amount of polymer-coupled peptidase.

For example, the sample can be taken from the blood of a patient who is being or has been treated with a drug containing an inhibitor of a peptidase of the hemostatic system as an active ingredient. After contacting the sample with the coupled peptidase, the inhibitor administered with the drug is bound by the peptidase and thus neutralized. Thus, within the framework of the method it is possible to also advantageously carry out tests on the sample after the inhibitor has been neutralized for the diagnosis of defects in the hemostatic system or for determining the activity of substances which affect the hemostatic system.

In patients who are treated with direct coagulation inhibitors, the presence of these inhibitors in the blood or plasma has the effect that certain in vitro laboratory methods for the diagnosis of the functional condition of the hemostatic system or for the determination of the activity of substances that affect the hemostatic system, are significantly biased and therefore no longer provide significant results. This especially applies to methods based on the measurement of the coagulation time from the moment specific activators are added until the onset of coagulation (e.g., aPTT, PT, TT, fibrinogen determination). Under the influence of the active ingredients in the drug, the coagulation time in these tests is already significantly delayed artificially and no longer allows for any diagnostic conclusions regarding the state of the hemostatic system. In particular, defective coagulation factors can no longer be diagnosed which is disadvantageous in various clinical situations. When the inhibitors are neutralized, these tests can be carried out without being affected by the inhibitor and retain their entire diagnostic validity.

For this embodiment as well, inhibitors are preferred which have a molecular weight of at least 100 Da and at most 10,000 Da. More preferred, the molecular weight of the inhibitor is at most 7,500 Da, in particular at most 5,000 Da or at most 2,500 Da. Examples of such inhibitors are mentioned above. For neutralizing the inhibitor according to the present invention, a polymer-coupled peptidase should advantageously be used on which the inhibitor acts as a direct inhibitor.

Another embodiment of the present invention is a device comprising a polymer-coupled peptidase of the hemostatic system according to the present invention for removing an inhibitor of a peptidase of the coagulation system from a sample or from the bloodstream of a patient. The polymer-coupled peptidase can for example be immobilized on a carrier material. As an example, reference is made in this connection to the document WO 98/46648 which discloses processes and interaction systems by means of which the polymer-coupled peptidases, in particular polyalkylene glycol or PEG-coupled peptidases, can be immobilized on a carrier material. The immobilization of the polymer-coupled peptidase can take place, for example, on particulate structures, capillaries, net structures or container walls. The immobilized coupled peptidase can in particular be present in a container, such as a cartridge, comprising an inlet and an outlet for liquids, through which a liquid can flow.

Especially suitable forms of the device are those which can be extracorporeally connected to the bloodstream of a patient.

For example, blood can be led extracorporeally—with or without a pump—by means of a tube system from the organism through a cartridge filled with a suitable material such as, for example, capillaries, particles or the like, on the surface of which the polymer-coupled peptidase is immobilized. When the blood (or plasma if a prior cell separation has been carried out) flows past the surface-immobilized polymer-coupled peptidase, it specifically binds the inhibitor contained therein which is thus removed from the circulation which leads to a decrease in the blood concentration to a non-toxic range.

In another embodiment, the present invention also encompasses a polymer-coupled peptidase of the hemostatic system according to the present invention for use in the restoration of the coagulability of blood, the increase of the coagulation tendency of blood and/or the acceleration of blood coagulation.

Such a use can in particular be indicated in patients who have been or are being treated with a low molecular coagulation inhibitor. Again, an inhibitor with a molecular weight of at least 100 Da and at most 10,000 Da is preferred. More preferred, the molecular weight of the inhibitor is at most 7,500 Da, in particular at most 5,000 Da or at most 2,500 Da. Examples of such inhibitors include active ingredients selected from the group of active ingredients of the drugs for the direct inhibition of coagulation factor Xa such as rivaroxaban, apixaban, betrixaban, otamixaban, edoxaban, raxazaban, eribaxaban, YM150, LY-517717 or PRT054021, or for the direct inhibition of thrombin such as dabigatran, argatroban, flovagatran, AZD0837, MCC-977, NU172 or bivalirudin.

Such polymer-coupled peptidases for neutralizing inhibitors, in particular direct low molecular weight coagulation inhibitors, can, for example, be used in patients, e.g., if the concentration of these substances in the blood are in a range that could lead to dangerous bleeding. For example, they can be used to allow surgery. For this purpose, the corresponding polymer-coupled peptidase can be administered directly to the bloodstream of the patient. In the blood, it will react specifically with the coagulation inhibitor and thus antagonize its anticoagulant effect without causing any effect itself. In contrast to mutants of coagulation factors, no risk of immunization exists since it can preferably be the native form of the protein. The example of hemophilia with inhibitors shows that even the slightest structural change resulting from point mutation can induce a clinically significant formation of antibodies. However, the polymer-coupled peptidase can also be brought in contact with the blood of a patient in immobilized form; in this connection, reference is made to the device disclosed above.

Finally, the present invention also relates to a test kit comprising a polymer-coupled peptidase of the hemostatic system as the first reagent, and a substrate of the peptidase as the second reagent which can be used in the methods and uses described above.

In particular, known substrates can be used in the kit from which the polymer-coupled peptidase can cleave a signal-generating group, such as e.g., a chromogenic substrate. Alternatively, fluorigenic, luminogenic or electrochemical substrates can be used as well. It should be understood that due to the modification of the peptidase according to the present invention, low molecular substrates are suitable for these purposes, preferably those having a molecular weight of at least 100 Da and at most 10,000 Da. More preferred, the molecular weight is at most 7,500 Da, in particular at most 5,000 Da or at most 2,500 Da.

The invention is described in more detail in the following examples, which are not intended to restrict the invention in any way.

Example 1

Preparation of a PEG-Factor Xa Conjugate

150 μg bovine factor Xa (EC 3.4.21.6, American Diagnostica Inc.), dissolved in 300 μl 10.05M phosphate buffer (pH 8.0) were added to 20 mg methoxy polyethylene glycol (PEG)-20,000 succinimidyl proprionate. The mixture was shaken at +2° C. to +8° C. for 1 hour. Subsequently, additional 10 mg methoxy-PEG-20,000 succinimidyl proprionate were added to the mixture followed by shaking at +2° C.-+8° C. for another hour.

Isolation of the PEG 20 kD-factor Xa conjugate was done by size exclusion chromatography using a Hi Load Superdex 200 pg 16/60 column with 0.02M Tris/HCl, 0.1M NaCl, pH 7.4 at a flow rate of 1 ml/min. At first, the PEG-factor Xa conjugate is eluted as a symmetric peak at an elution volume of 40 ml (detection of UV absorption at 220 nm and 280 nm). The excess of polymer as well as the reaction products are eluted later which made it possible to separate them from the conjugated protein.

Protein containing fractions showing factor Xa activity (measured via the cleavage of a chromogenic substrate specific for factor Xa) were collected in fraction collecting tubes containing PEG 8000 for stabilisation. Fractions containing the highest activity of factor Xa were pooled and stored in aliquots at −80° C.

Example 2

Enzymatic Properties of PEG 20 kD-Factor Xa Conjugate a) Cleavage of Chromogenic Substrate by PEG 20 kD-Factor Xa Conjugate The capability to cleave the chromogenic substrate N-α-Z-D-Arg-Gly-Arg-pNA (Haemochrom Diagnostica GmbH) was characterized by determination of the Michaelis-Menten constant $K_m$ of the substrate. Its $K_m$-value for PEG 20 kD-factor Xa conjugate was found to be 0.102 mM, which is identical with the $K_m$-value for the unmodified factor Xa, which was found to be 0.106 mM.

b) Inhibition of the Amidolytic Activity of PEG 20 kD-Factor Xa Conjugate by the Low Molecular Weight Direct Inhibitor Pefabloc Xa.

To determine the inhibition of the amidolytic activity of PEG 20 kD-factor Xa conjugate by the low molecular weight direct inhibitor Pefabloc Xa (Loxo GmbH), a chromogenic assay was used. Assessment of the results was done according to Lineweaver-Burk. The inhibition constant $K_i$ of Pefabloc Xa related to PEG 20 kD-factor Xa conjugate was found to be 0.7±0.13 μM which is comparable to the value determined for the unmodified enzyme ($K_i$: 1.1±0.07 μM).

c) Influence of Antithrombin and Heparin/Antithrombin on the Amidolytic Activity of PEG 20 kD-Factor Xa Conjugates 25 μl factor Xa (American Diagnostica Inc., 1 μg/ml) and PEG 20 kD-factor Xa conjugate (1 μg protein/ml), respectively, were incubated with 25 μl antithrombin III (50 units/ml, Sigma Chemical Co. A-7388) for 2 to 20 min. After incubation, chromogenic substrate was added and the amidolytic activity was determined. The activity of factor Xa was inhibited by 99% depending on the incubation time, whereas antithrombin III was without inhibitory effect on PEG 20 kD-factor Xa conjugate activity (FIG. 1).

Figure 2:
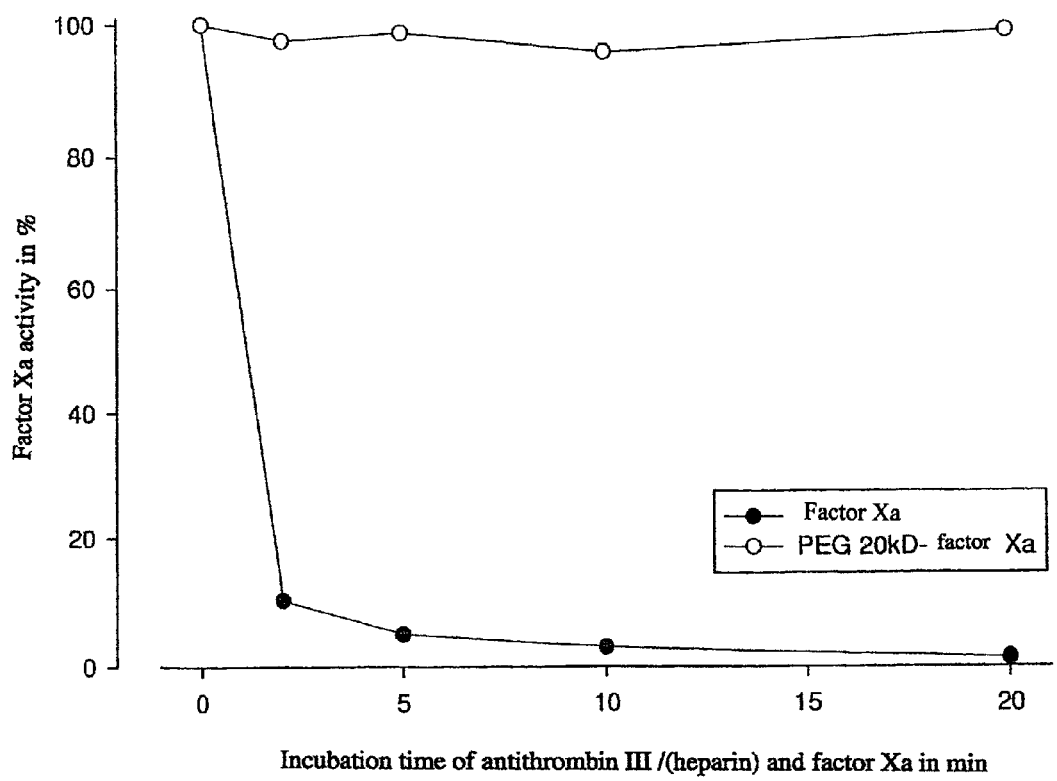
FIG. 2: Influence of incubation with antithrombin III/heparin (low molecular weight) on the activity of PEG 20 kD-factor Xa conjugate and non-modified factor Xa, respectively.

25 µl factor Xa (American Diagnostica Inc., 1 µg/ml) and PEG 20 kD-factor Xa conjugate (1 µg protein/ml), respectively, were incubated with 25 µl of a mixture made from antithrombin (10 units/ml, Sigma Chemical Co. A-7388) and heparin (2 anti-FXa units/ml, low molecular weight heparin, 2nd International Standard, NIBSC) for 2 to 20 min. After incubation, chromogenic substrate was added and the amidolytic activity was determined. The activity of factor Xa was inhibited by 99% depending on the incubation time, whereas the antithrombin III-heparin complex was without inhibitory effect on PEG 20 kD-factor Xa conjugate activity (FIG. 2).

d) Activity of PEG 20 kD Factor Xa in the Plasmatic Coagulation System

In order to determine coagulation activity of unmodified factor Xa (American Diagnostica Inc.) 50 µl plasma were incubated with 50 µl factor Xa (protein content between 0.015 µg/ml and 2 µg/ml) at 37° C. for 1 min. Coagulation process was started by addition of 50 µl 0.025M $CaCl_2$ solution prewarmed to 37° C. Coagulation time was measured using the ball coagulometer KC4A Micro. Values of clotting time were found to be between 178 s and 34 s.

If PEG 20 kD-factor Xa conjugate was used instead of unmodified factor Xa in the same concentration range no clotting was induced. All of the measured clotting times were above 250 s.

Figure 3:
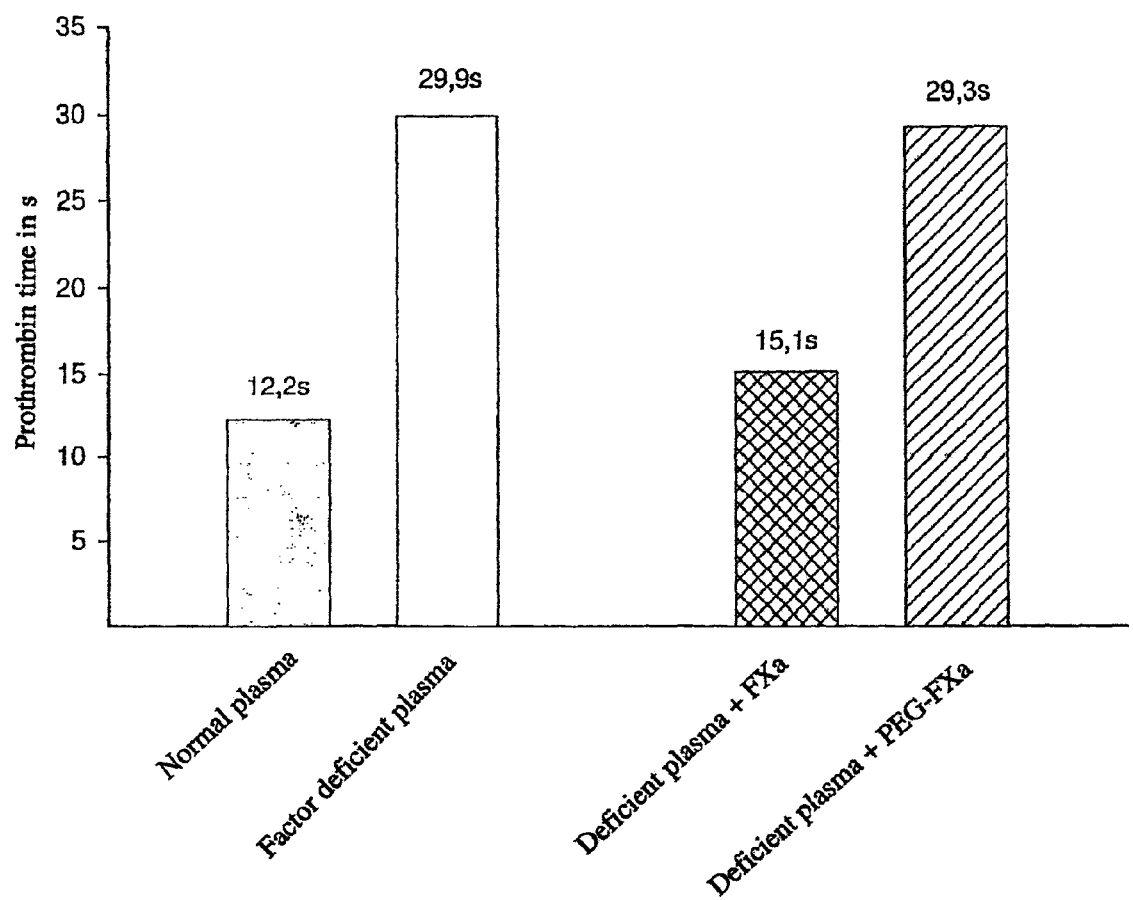
FIG. 3: Influence of the addition of PEG 20 kD-factor Xa conjugate and non-modified factor Xa, respectively, on the prothrombin time measured in plasma depleted of coagulation factors.

To demonstrate that PEG 20 kD-factor Xa shows no activity in the coagulation system the following experiments were carried out: Factor Xa and PEG 20 kD-factor Xa conjugates, respectively, were added to plasma depleted of coagulation factors (abnormal plasma, American Diagnostica Inc). If factor Xa was added (50 µl plasma+50 µl 8 µg/ml factor Xa in 1.5% BSA), a prothrombin time of 15.1 s was measured which was lower than the 29.9 s measured in the abnormal plasma without factor Xa addition (prothrombin time in normal plasma, American Diagnostica Inc.: 12.2 s). This was caused by the compensation of factor Xa deficiency in the abnormal plasma. Addition of the same amount of PEG 20 kD-factor Xa conjugate did not reduce the prothrombin time in the abnormal plasma. The PEG 20 kD-factor Xa conjugate showed no activity in the plasmatic coagulation system (FIG. 3).

Example 3

Quantitative Determination of the Low Molecular Weight Synthetic Direct Factor Xa Inhibitor Pefabloc Xa in Plasma For quantitative determination of the direct synthetic factor Xa inhibitor Pefabloc Xa (Loxo GmbH) in plasma 25 µl PEG 20 kD-factor Xa conjugate (1 µg/ml in 0.02M Tris/HCl, 0.1M NaCl, 1.5% PEG 8,000, pH 7.4 at room temperature), 25 µl plasma sample (citrated plasma) and 100 µl reaction buffer (0.05M Tris/HCl, 0.3M NaCl, pH 8.4 at room temperature) were incubated at 37° C. in the measurement device (TC4+, TECO GmbH) for 1 min. After addition of 50 µl chromogenic substrate the increase in optical density was recorded at 405 nm (release of p-nitroaniline by cleavage of the chromogenic substrate by the non-inhibited part of PEG 20 kD-factor Xa conjugate).

Figure 4:
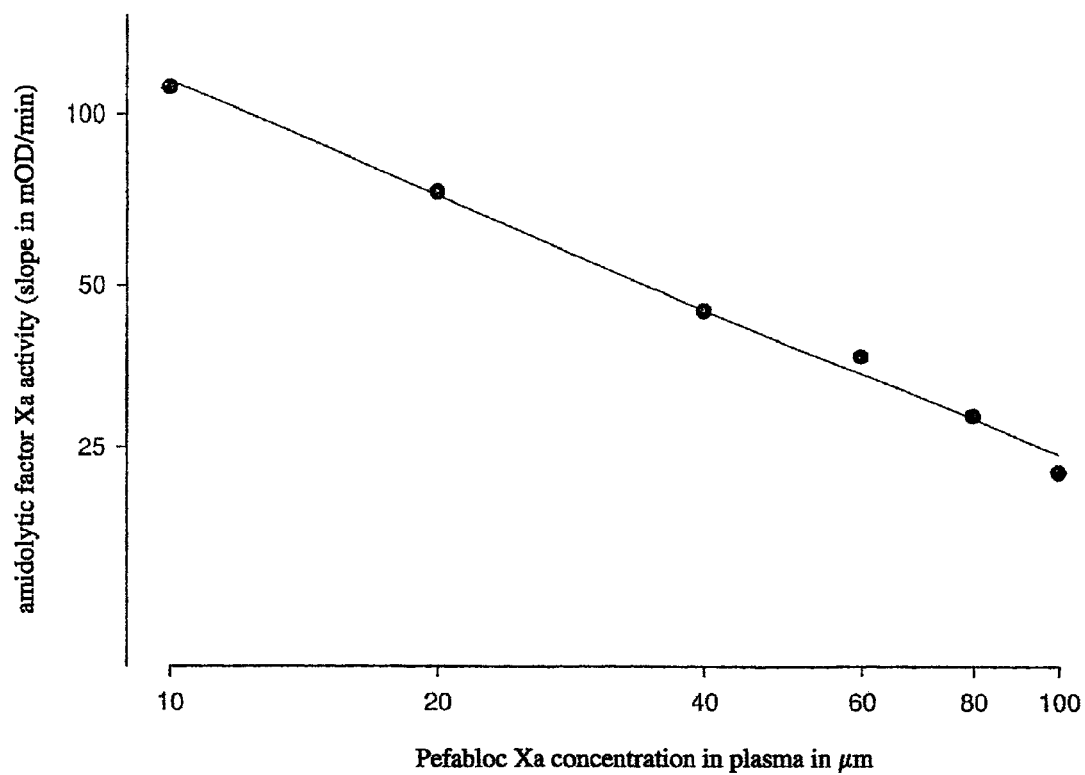
FIG. 4: Reference curve for quantitative determination of the direct factor Xa inhibitor Pefabloc Xa in plasma using the chromogenic PEG-factor Xa assay.

Activity of PEG 20 kD-factor Xa conjugate was calculated using the slope of the reaction curves (change in optical density in mOD/min). Activity decreases in proportion to the plasma concentration of the inhibitor. A reference curve was created by measuring the activity of the PEG 20 kD-factor Xa conjugate in the presence of defined concentrations of the inhibitor (10 µM-100 µM) in pooled citrated plasma (FIG. 4). Using this reference curve, unknown inhibitor concentrations can be determined in plasma samples via inhibitor activity.

Example 4

Preparation of PEG-Factor IIa Conjugate 5 mg bovine factor IIa (thrombin, EC 3.4.21.5, Kordia) and 100 mg methoxy polyethylene glycol (PEG)-5,000 p-nitrophenyl carbonate were dissolved in 500 µl 0.05M phosphate buffer, pH 8.0. The mixture was shaken at +2° C. to +8° C. for 2 h. During time of shaking further amounts of methoxy polyethylene glycol (PEG)-5,000 p-nitrophenyl carbonate were added after 30 min (45 mg), 60 min (45 mg) as well as after 90 min (6 mg).

Isolation of the PEG 5 kD-thrombin conjugate was done by size exclusion chromatography using a Hi Load Superdex 200 pg 16/60 column with 0.1M NaCl at a flow rate of 1 ml/min. At first, the PEG 5 kD-thrombin conjugate is eluted as a symmetric peak at an elution volume of 55 ml (detection of UV absorption at 220 nm and 280 nm). The excess of polymer as well as the reaction products are eluted later which made it possible to separate them from the conjugated protein.

Protein containing fractions were collected in fraction collecting tubes containing PEG 8,000 for stabilisation. Fractions containing the highest activity of thrombin (measured via the cleavage of a chromogenic substrate specific for thrombin) were pooled and stored in aliquots at −20° C.

Example 5

Quantitative Determination of the Low Molecular Direct Factor IIa Inhibitor Argatroban in Plasma For quantitative determination of the direct synthetic factor II inhibitor argatroban (Mitsubishi Pharma) in plasma, 15 µl plasma sample (citrated plasma) were added to 50 µl chromogenic substrate (H-D-Chg-Ala-Arg-pNA, JenAffin GmbH, 3 mM in 0.05M Tris/HCl, 0.1M NaCl, pH 8.0 at 37° C.). Chromogenic reaction was started by addition of 100 µl PEG 5 kD-thrombin conjugate. Increase in optical density (release of p-nitroaniline by cleavage of the chromogenic substrate by the non-inhibited part of PEG 5 kD-thrombin conjugate) was recorded at 405 nm using the measurement device TC4+ (TECO GmbH).

Figure 5:
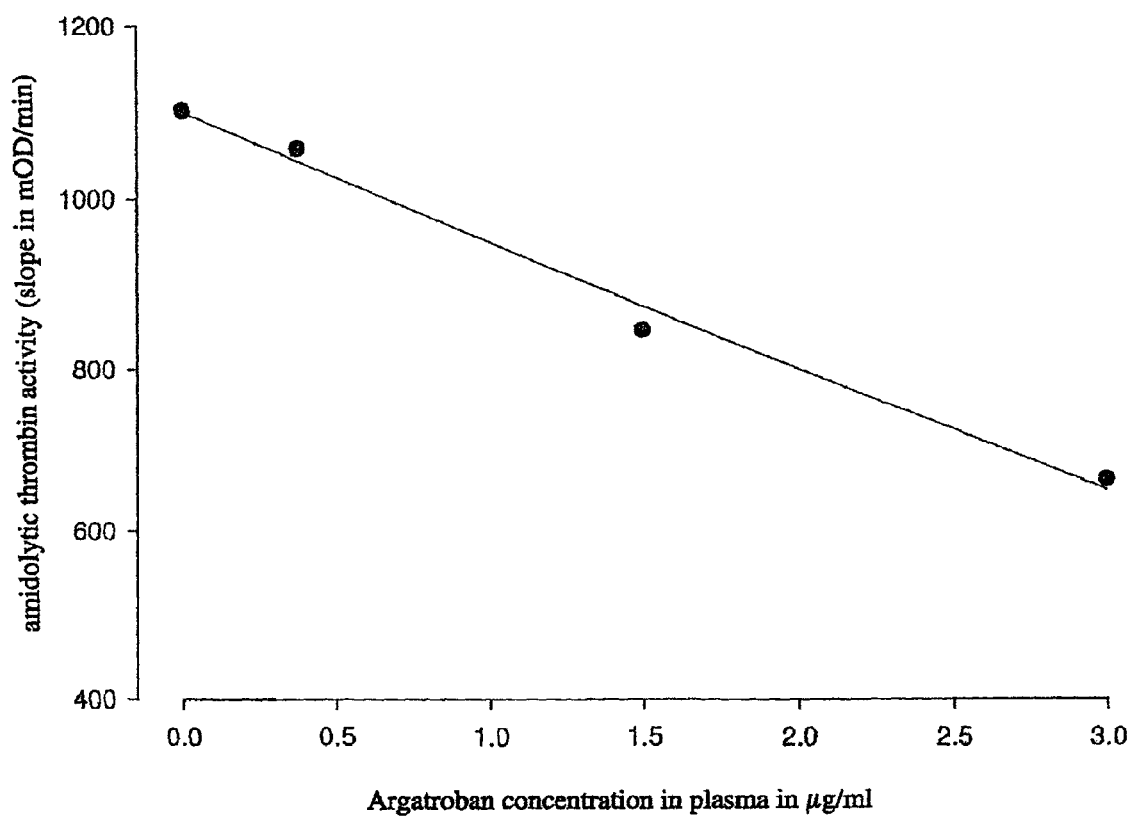
FIG. 5: Reference curve for quantitative determination of the direct thrombin inhibitor argatroban in plasma using the chromogenic PEG-thrombin assay.

Activity of the PEG 5 kD-thrombin conjugate was calculated using the slope of the reaction curves (change in optical density in mOD/min). Activity decreases in proportion to the plasma concentration of the inhibitor. A reference curve was created by measuring the activity of PEG 5 kD-thrombin conjugate in the presence of defined concentrations of the inhibitor (0.375 µg/ml-3 µg/ml) in pooled citrated plasma (FIG. 5). Using this reference curve, unknown inhibitor concentrations can be determined in plasma samples via the inhibitor activity.

Example 6

Influence of Heparin on the Amidolytic Activity of PEG 5 kD-Thrombin Conjugate

The influence of heparin (Sigma, H-3393) on the amidolytic activity of PEG 5 kD-thrombin conjugate in plasma was compared with its influence on the amidolytic activity of unmodified thrombin using the chromogenic assay for quantitative determination of direct thrombin inhibitors (Example 5): 15 µl of a plasma sample (citrated plasma) were added to 50 µl chromogenic substrate (H-D-Chg-Ala-Arg-pNA, JenAffin GmbH, 3 mM in 0.05M Tris/HCl, 0.1M NaCl, pH 8.0 at 37° C.). Chromogenic reaction was started by addition of 100 µl PEG 5 kD-thrombin conjugate or thrombin, respectively. Increase in optical density (release of p-nitroaniline by cleavage of the chromogenic substrate) was recorded at 405 nm using the measurement device TC4+ (TECO GmbH).

It could be shown that increasing concentrations of heparin in the plasma sample (heparin in combination with antithrombin of plasma) inhibit amidolytic activity of thrombin but does not influence amidolytic activity of PEG 5 kD-thrombin conjugate (FIG. 6).

The invention claimed is:

1. A method for the detection or quantitative determination of an inhibitor of a peptidase of the hemostatic system in a sample, comprising the steps of bringing the inhibitor in the sample into contact with a polymer-coupled native peptidase of the hemostatic system or a polymer-coupled fragment or mutant thereof, which fragment or mutant, before being coupled to the polymer, shows the same physiological effect and interacts with the same substances as the corresponding native peptidase, resulting in the same biological effect, wherein the specificity of the native peptidase or fragment or mutant thereof is modified via the polymer coupling such that the native peptidase or fragment or mutant thereof loses its reactivity in the hemostatic system, but is still able to react with inhibitors and substrates of low molecular weight, and measuring the activity of the polymer-coupled native peptidase or fragment or mutant thereof after it has been brought into contact with the inhibitor in the sample.

2. The method according to claim 1, further comprising the step of comparing the activity of the polymer-coupled native peptidase or fragment or mutant thereof measured after it has been brought into contact with the sample with one or more reference values of the activity of the polymer-coupled native peptidase or fragment or mutant thereof.

3. The method according to claim 2, wherein the one or more reference values are obtained from samples containing the polymer-coupled native peptidase or fragment or mutant thereof without the inhibitor and/or together with known concentrations of the inhibitor.

4. The method according to claim 1, wherein the sample is a bodily fluid, selected from blood, plasma, serum, liquor and sweat.

5. The method according to claim 1, wherein the inhibitor is a direct inhibitor of the peptidase of the hemostatic system, preferably an inhibitor with a molecular weight between 100 and 7,500 Da.

6. The method according to claim 1, wherein the inhibitor is an active ingredient of the classes of direct factor Xa inhibitors or direct thrombin inhibitors.

7. The method according to claim 1, wherein the peptidase of the hemostatic system is a coagulation factor selected from the group consisting of factor IIa (thrombin), VIIa, IXa, Xa, XIa and fragments and mutants of these factors.

8. The method according to claim 1, wherein the peptidase of the hemostatic system is factor IIa (thrombin) or factor Xa.

9. The method according to claim 1, wherein the polymer is a polyalkylene glycol or a copolymer comprising alkylene glycol units.

10. The method according to claim 1, wherein the polymer is polyethylene glycol or a copolymer comprising ethylene glycol units.

11. A method for the complete or proportional inhibition of the activity of an inhibitor of a peptidase of the hemostatic system, comprising the step of bringing a sample containing the inhibitor into contact with a polymer-coupled native peptidase of the hemostatic system or a polymer coupled fragment or mutant thereof, which fragment or mutant, before being coupled to the polymer, shows the same physiological effect and interacts with the same substances as the corresponding native peptidase, resulting in the same biological effect, wherein the specificity of the native peptidase or fragment or mutant thereof is modified via the polymer coupling such that the native peptidase or fragment or mutant thereof loses its reactivity in the hemostatic system, but is still able to react with inhibitors and substrates of low molecular weight, and measuring the inhibition of the polymer-coupled native peptidase or fragment or mutant thereof after it has been brought into contact with the inhibitor in the sample.

12. The method according to claim 11, wherein the sample is taken from the blood of a patient who is being or has been treated with a drug containing an inhibitor of a peptidase of the hemostatic system as an active ingredient and wherein, after the sample has been brought into contact with the polymer-coupled native peptidase or fragment or mutant thereof, the inhibitor administered with the drug is bound by the polymer-coupled native peptidase or fragment or mutant thereof and thus neutralized.

13. The method according to claim 12, wherein additionally, after neutralization of the inhibitor, tests are carried out on the sample in order to diagnose defects in the hemostatic system or to determine the activity of substances which interfere with the hemostatic system.

14. The method according to claim 12, wherein the complete or proportional neutralization of the inhibitor of a peptidase of the hemostatic system is carried out in order to achieve a restoration of the coagulation ability of the blood of a patient who has been treated or is being treated with a pharmaceutical composition containing an inhibitor of a peptidase of the hemostatic system, and wherein the neutralization comprises contacting the polymer-coupled native peptidase or fragment or mutant thereof with the inhibitor in the circulation of the patient.

15. The method according to claim 11, wherein the sample is a bodily fluid, selected from blood, plasma, serum, liquor and sweat.

16. The method according to claim 11, wherein the inhibitor is a direct inhibitor of the peptidase of the hemostatic system, preferably an inhibitor with a molecular weight between 100 and 7,500 Da.

17. The method according to claim 11, wherein the peptidase of the hemostatic system is a coagulation factor selected from the group consisting of factor IIa (thrombin), VIIa, IXa, Xa, XIa and fragments and mutants of these factors.

18. The method according to claim 11, wherein the polymer is a polyalkylene glycol or a copolymer comprising alkylene glycol units.

19. The method according to claim 11, wherein a defined amount of the polymer-coupled native peptidase or fragment or mutant thereof is added to the sample to achieve a proportional neutralization of the inhibitor by contacting the inhibitor in a sample with the polymer-coupled native peptidase or fragment or mutant thereof, and the remaining activity of the inhibitor in the sample as a measure for the initial concentration is determined in terms of the influence of the inhibitor on the coagulation tendency by carrying out a coagulation test in the sample, including the addition of a coagulation activator and optionally normal plasma as a source for additional coagulation factors and fibrinogen.

20. The method according to claim 11, further comprising measuring the activity of the polymer-coupled native peptidase or fragment or mutant thereof after it has been brought into contact with the inhibitor in the sample.

21. The method according to claim 20, further comprising the step of comparing the activity of the polymer-coupled native peptidase or fragment or mutant thereof measured after it has been brought into contact with the sample with one or more reference values of the activity of the polymer-coupled native peptidase or fragment or mutant thereof.

22. The method according to claim 21, wherein one or more reference values are obtained from samples containing the polymer-coupled native peptidase or fragment or mutant thereof without the inhibitor and/or together with known concentrations of the inhibitor.

23. The method according to claim 11, wherein the inhibitor is an active ingredient of the classes of direct factor Xa inhibitors or direct thrombin inhibitors.

24. The method according to claim 11, wherein the peptidase of the hemostatic system is factor IIa (thrombin) or factor Xa.

25. The method according to claim 11, wherein the polymer is polyethylene glycol or a copolymer comprising ethylene glycol units.

* * * * *